(12) United States Patent
Messner et al.

(10) Patent No.: US 6,475,566 B1
(45) Date of Patent: Nov. 5, 2002

(54) PROCESSING FOR IMPROVING THE IMPREGNABILITY OF WOOD BY PRETREATMENT WITH FUNGI

(75) Inventors: Kurt Messner, Vienna (AT); Vinzenz Fleck, Frohnleiten (AT); Alan Bruce, Dundee (GB); Bernhard Rosner, Vienna (AT)

(73) Assignee: Lignocell Holz-Biotechnologie Gesellschaft m.b.H., Vienna (AT)

( * ) Notice: Subject to any disclaimer, the term of this patent is extended or adjusted under 35 U.S.C. 154(b) by 0 days.

(21) Appl. No.: 09/528,699

(22) Filed: Mar. 17, 2000

(51) Int. Cl.$^7$ .................................................. B05D 3/00
(52) U.S. Cl. ....................... 427/325; 427/308; 427/324; 427/393; 427/397; 427/444; 427/317
(58) Field of Search ................................ 427/308, 317, 427/324, 325, 393, 393.4, 397, 444

(56) References Cited

U.S. PATENT DOCUMENTS

| | | | |
|---|---|---|---|
| 3,486,969 A | | 12/1969 | Nilsson et al. |
| 5,055,159 A | * | 10/1991 | Blanchette et al. ........... 162/72 |
| 5,620,564 A | * | 4/1997 | Akhtar ........................ 162/72 |

FOREIGN PATENT DOCUMENTS

| | | | |
|---|---|---|---|
| DE | 292 864 | | 8/1991 |
| EP | 0 001 540 A | | 4/1979 |
| EP | 1540-a | * | 4/1979 |
| FR | 2705607-a | * | 12/1994 |
| FR | 2 705 607 | | 12/1994 |
| GB | 2 239 800 A | | 7/1991 |
| RU | 507677-a | * | 4/1976 |
| WO | WO93/08694 | | 5/1993 |

* cited by examiner

*Primary Examiner*—Brian K. Talbot
(74) *Attorney, Agent, or Firm*—Baker Botts LLp

(57) ABSTRACT

The object of the invention is a method for improving the impregnability of refractory wood species by pretreatment with fungi of the genera Trichoderma o Gliocladium or with weakly wood-degraging fungi. The pretreatment comprises a thermal treatment of the wood, the addition of a nutrient medium as well as an incubation phase to promote fungal growth. The incubation phase is stopped when the desired depth of penetration of the fungus is reached. The wood is subsequently impregnated with a wood impregnating agent. The typical result of the fungal pretreatment is an incarease in the depth of penetration of the impregnating agent to a depth of penetration of 5 mm to 30 mm required depending on the intended use.

17 Claims, No Drawings

PROCESSING FOR IMPROVING THE IMPREGNABILITY OF WOOD BY PRETREATMENT WITH FUNGI

TECHNICAL FIELD

The invention describes a method for improving the impregnability of wood. Various wood species, such as spruce, Douglas fir, fir, oak or acacia, are characterized by favourable properties, such as resistance to checking and splitting as well as low distortion and torsion, straight fibers and minimal branching. These wood species are not widely used because they are difficult to impregnate with chemicals. This is generally true of the heart wood of all wood species. Even if the most efficient impregnating methods are used in wood protection, a wood preservative frequently does not penetrate deeper than 2–3 mm, while the standards in wood protection for timber in European hazard class IV (Ground Contact Timbers) call for a depth of penetration of at least 5–10 mm and of 6–30 mm for poles. For example an uptake of at least 63 kg of creosote/$m^3$ of wood is required for palisades and of 90 kg/$m^3$ for poles (figure for U.K. is 115 Kg/$m^3$). This limit cannot be reached with the above-mentioned refractory wood species without additional pre-treatment At present the method of pretreatment most frequently used in wood protection is the very costly incising method according to which 3 cm deep holes spaced 4–8 mm apart are cut into the base of the pole or throughout the sawn timber member in order to promote the penetration of the wood preservative.

The reason for the poor impregnability is the behaviour of the pits during wood drying. Pits are connective openings between the wood cells which permit water transport. The anatomy of the pits is such that the two cell walls on either side of the middle lamella form a dome-shaped cavity and each has an opening called a pore. At this point the middle lamella is thickened to form the so-called torus. When the wood is dried, this thickened portion attaches to the border of the pore and seals it irreversibly in refractory wood species. The chemical background of this process has not been ascertained yet.

BACKGROUND ART

At present the most common method of improving the impregnability of wood by wood preservatives is the wet storage of wood in ponds for a period of several months, which promotes the development of bacterial populations that open the pits. However, this process cannot be controlled and leads to irregular results.

A more modem version of this method was developed for the pretreatment of pulpwood in which a mixture of selected strains of bacteria is used and which is said to result in a reduction of blue stain and resin degradation as well as reduction of the cooking time (WO 9636765). A similar effect is achieved in pulping also by pretreating wood chips with the fungus *Ophiostoma piliferum* (Blanchette, Farrell and Burnes 1992, Tappi 75, 102–106).

In wood protection attempts have been made to restore the pit passage by the action of a pectinolytic enzyme preparation (German Patent DD 292 864 A5). The disadvantage of these processes is that they are designed to degrade only one particular component of the pits, such as pectin, however apparently several components, not yet determined, are responsible for the pit closure.

DISCLOSURE OF THE INVENTION

The subject of the invention is a biological process in which the impregnability of the wood by wood preservatives is improved by growing fungi on the wood. Preferably fungi of the genus Trichoderma, such as *Trichoderma viride* SIWT T70, *Trichoderma aureoviride* SIWT T1 or the strains *Trichoderma harzianum* LC1, LC2, *Hypocrea piluliferum* LC3, or *Gliocladium roseum* LC4 as well as weakly wood-degrading fungi, such as *Phanerochaete chrysosporium* LC5 or *Dichomitus squalens* LC6 are employed. In the latter case these fungi are eradicated after incubation.

The use of living wood-colonizing fungi has the advantage over the use of enzyme solutions in that enzyme solutions have to be applied by a separate impregnating process, which poses a problem in particular with refractory wood species, whereas fungi may actively grow into the wood with the help of their filamentous hyphae. Another advantage of fungi is that they excrete the necessary mixture of enzymes and other low molecular size agents in the vicinity of the pits, which is required for the opening of the pit passages, but the composition of which has not been determined yet.

The inventive feature of the present process is that for improving the impregnability of wood it is inoculated with selected strains of fungi of the genus Trichoderma or Gliocladium, or with strains selected from the group of weakly wood-degrading fungi which are particularly suited to improve the uptake of the impregnating agent by the wood. Use of selected strains of Trichoderma or Gliocladium cause no decrease in strength of the timber and additionally have the effect of biological wood protection, for example *Trichoderma harzianum* LC1, LC2, *Hypocrea piluliferum* LC3 (EP 0 615 409 B1). The use of weakly wood-degrading fungi only results in limited damage to the wood during the period of treatment (usually below 10% strength loss).

According to the invention the weakly wood-grading fungi are eradicated after pretreatment as soon as the desired impregnating aim is achieved to avoid extended damage to the wood.

The decontaminating and growth promoting measures prior to inoculation enable the applied strains of fungi to rapidly grow into the wood without any appreciable competition by other organisms and to perform their pit opening activity there. The process makes it possible to use also wood species which are difficult to impregnate without expensive and time consuming mechanical pretreatment processes, such as the incising method, in the same fields of application as easily impregnable wood species thereby significantly expanding the market for such species.

BEST MODE FOR CARRYING OUT THE INVENTION

The method includes a decontamination stage prior to the application of the biological agent to the timber. This stage may not be required however dependant on the timing of the treatment after felling of the timber. A principle of the method according to the invention is to promote the fungal growth preferably (though not essentially) by thermal decontamination of the wood surface prior to inoculation and by the addition of a growth promoting medium. The decontamination of the wood surface is effected preferably by steam at 100–120° C. for 10 seconds–30 minutes, depending on the degree of contamination, followed by a cooling phase. The growth promoting medium may be applied separately or jointly with the fungal inoculum. It contains preferably a diluted suspension of cornsteep liquor.

According to the invention inoculation is effected in the case of sporulating fungi, such as the Trichoderma and Gliocladium species, by applying a spore suspension, and in the case of non-sporulating fungi, such as basidiomycetes, by applying a mycelium suspension to the wood surface. The inoculating suspension may be applied by spraying, dipping, brushing, etc., the inoculum concentration should exceed 100 colony-forming units/ml.

The incubating phase ideally takes place at the optimum temperature of the respective fungus employed and ranges from 10 to 50° C., but preferably from 20 to 30° C. It may be stopped as soon as the desired depth of penetration of the fungus and the resulting opening of the pits is reached. This objective is reached—depending on the strain of fungus—after a few days to 4 weeks at the most. The resulting loss of wood strength ranges from 0% for Trichoderma or Gliocladium species to no more than 10% for weakly degrading basidiomycetes depending on the fungal strain (see results table).

If weakly wood-degrading fungi are used, the fungus grown into the wood is eradicated according to the invention at the end of incubation. This may be done, depending on the type of method used, either in the course of wood drying in drying kilns at elevated temperatures of 40–100° C. or by steaming of the wood at 100–120° C. or by a fungicide applied after fungal colonisation. Furthermore, the fungus may be eradicated in the course of pressure treatment in which temperatures of up to 160° C. are reached.

The subsequent impregnating process may be a pressure treatment (high pressure or low pressure process), non-pressure treatment (dip treatment), or special process. The impregnating agents to be employed are not limited to wood preservatives, but comprise all chemical substances designed for impregnation, such as fire protectants, synthetic resins, and chemicals designed for wood modification etc.

Example:

Spruce logs stripped of the bark (Picea abies, 1 m length, 100 to 200% wood moisture content) were subjected to a decontamination treatment by steaming for 10 minutes and were subsequently cooled down to ambient temperature.

The inoculum fungi *Trichoderma viride* SIWT T70, *Trichoderma aureoviride* SIWT T1, *Trichoderma harzianum* LC1, *Trichoderma harzianum* LC2, *Trichoderma harzianum* LC3, *Gliocladium roseum* LC4, *Phanerochaete chrysosporium* LC5 *Dichomitus squalens* LC6, were grown in Petri dishes on 2% malt agar and blended in a sterile mixer in a 2% solution of cornsteep liquor. The concentrated fungal suspensions were diluted in a growth promoting medium containing cornsteep liquor and were used as an inoculum. Inoculation was effected by dipping 10 spruce logs into the microbial inoculum of each test fungus in the respective mycelium suspension. The strains were subsequently incubated in rooms with constant climate at the optimum temperatures for each test fungus for 1, 2, 3 or 4 weeks, respectively.

After the incubation period the spruce logs were dried in a drying kiln at temperatures between 50 and 65° C. for a period of 12 days to 10–20% wood moisture content. Ten logs not inoculated with fungi were dried under the same conditions to serve as controls.

The pretreated logs and the controls were impregnated with creosote in the same way according to an industrial pressure treatment process designed for pine wood They were subsequently cut apart and the depth of penetration measured. Additionally test wood blocks were cut out and subjected to strength tests (ISO Standard No.3349) as well as analyzed for the loading of the wood preservative.

Results:

|  | weeks of incubation | depth of penetration (cm) | creosote loading kg/m³ | strength loss (%) |
|---|---|---|---|---|
| SIWT T70 | 3 | 2,7–3,0 | 150 | 0 |
| SIWT T1 | 3 | 2,0–2,7 | 160 | 0 |
| T. harz. LC1 | 3 | 2,5–2,9 | 160 | 0 |
| T. harz. LC2 | 3 | 2,0–2,7 | 155 | 0 |
| H. pil. LC3 | 3 | 2,6–3,0 | 160 | 0 |
| Gl. ros. LC4 | 3 | 2,1–2,9 | 160 | 0 |
| Ph. chr. LC5 | 1 | 2,3–3,0 | 240 | 0 |
|  | 2 | 2,3–3,2 | 260 | 10 |
|  | 3 | 2,5–3,2 | 260 | 10 |
| D. squ. LC6 | 1 | 1,0–1,5 | 130 | 0 |
|  | 2 | 2,3–2,8 | 150 | 10–15 |
|  | 3 | 2,3–3,0 | 250 | 10–15 |
| Controls |  | 0,15–0,95 | *) | 0 |

*) cannot be tested because penetration is not deep enough.

A depth of penetration of 2–3 cm correlates with a total penetration of the sap wood area of the logs with creosote.

Industrial Applicability

The method according to the invention is applicable in all those areas in which the capablity of certain wood species to take up any impregnating agent does not guarantee a particular quantity of uptake or depth of penetration. The main field of application is wood protection, as e.g. when using spruce wood (Picea spp.) for poles or palisades. Without any prior opening of the pit passages and clearing of blockage materials in the ray parenchyma tissues the uptake of the wood preservatives required for protection of timber in soil contact situations can only be reached by very costly conventional physical processes. Preservative treatment levels required to meet national standards can however be achieved by the pretreatment according to the invention. Similarly, sawn construction timbers can be more properly treated with preservatives using the method.

However, the invention also extends to the impregnation of wood with other impregnating agents, such as synthetic resins, or to agents for the chemical modification of wood.

What is claimed is:

1. A method for improving the impregnability of wood to a chemical, comprising colonizing the wood with a fungus or mixture of fungi, wherein the fungi are selected from the group consisting of Basidomycetes, Ascomycetes and Deuteromycetes.

2. The method of claim 1, comprising colonizing the wood with a mixture of fungi and other micro-organisms.

3. The method of claim 1, wherein the fungi are selected from among Trichoderma or Gliocladium strains.

4. The method of claim 3, wherein the Trichoderma is in a teleomorphic state.

5. The method of claim 3, wherein the fungi are selected from the group consisting of *Trichoderma viride* SI WT T70, *Trichoderma aureviride* SI WT T1, *Trichoderma harzanium* LC1, *Trichoderma harzanium* LC2, and *Hypocrea piluliferum* LC3.

6. The method of claim 3, wherein the fungi are *Gliocladium roseum* LC4.

7. The method of claim 1, wherein the fungi are selected from the group consisting of *Phanerochaete chrysosporium* LC5 and *Dichomitus squalens* LC6.

8. The method of claim 1, further comprising decontaminating the wood prior to colonizing.

9. The method of claim 8, wherein decontaminating comprises a chemical or thermal pretreatment.

10. The method of claim 9, wherein decontaminating comprises subjecting the wood to steam at a temperature of from 100–120° C., followed by cooling.

11. The method of claim 1, further comprising colonizing the wood in the presence of a fungal growth promoting medium.

12. The method of claim 11, wherein the growth promoting medium contains cornsteep liquor.

13. The method of claim 1, further comprising inoculating the wood with the fungi and incubating the fungi-inoculated wood at a temperature adapted to fungal growth.

14. The method of claim 13 wherein the temperature is from 10–50° C.

15. The method of claim 14, wherein the temperature is from 20–30° C.

16. The method of claim 1, further comprising eradicating the fungi after colonizing the wood.

17. The method of claim 10, wherein the fungi are eradicated by heating the colonized wood.

* * * * *

UNITED STATES PATENT AND TRADEMARK OFFICE
CERTIFICATE OF CORRECTION

PATENT NO. : 6,475,566 B1
DATED : November 5, 2002
INVENTOR(S) : Messner et al.

It is certified that error appears in the above-identified patent and that said Letters Patent is hereby corrected as shown below:

<u>Title page,</u>
Item [57], ABSTRACT,
Line 3, "o" should read -- or --
Line 4, "wood-degraging" should read -- wood-degrading --
Line 10, "incarease" should read -- increase --
Item [74], *Attorney, Agent or Firm,* "LLp" should read -- LLP --

<u>Column 1,</u>
Line 21, "Kg/m$^3$)." should read -- kg/m$^3$). --
Line 49, "modem" should read -- modern --

<u>Column 2,</u>
Line 34, "wood-grading" should read -- wood-degrading --
Line 53, "dependant" should read -- dependent --

<u>Column 3,</u>
Line 2, "basidiomycetes," should read -- Basidiomycetes, --
Line 16, "basidiomycetes" should read -- Basidiomycetes --
Line 63, "wood They" should read -- wood. They --

<u>Column 4,</u>
Line 25, "capablity" should read -- capability --
Line 46, "Basidomycetes" should read -- Basidiomycetes --
Lines 56 and 57, "harzanium" should read -- harzianum --

UNITED STATES PATENT AND TRADEMARK OFFICE
CERTIFICATE OF CORRECTION

PATENT NO.    : 6,475,566 B1
DATED         : November 5, 2002
INVENTOR(S)   : Messner et al.

It is certified that error appears in the above-identified patent and that said Letters Patent is hereby corrected as shown below:

Column 6,
Line 7, "claim 10," should read -- claim 16, --

Signed and Sealed this

Fifteenth Day of February, 2005

JON W. DUDAS
*Director of the United States Patent and Trademark Office*